(12) United States Patent
Schmitz

(10) Patent No.: US 11,737,656 B2
(45) Date of Patent: Aug. 29, 2023

(54) CATHETER AND TUBE INTRODUCER

(71) Applicant: PatCom Medical Inc., Toronto (CA)

(72) Inventor: Christoph Burkhard Schmitz, Toronto (CA)

(73) Assignee: PatCom Medical Inc., Etobicoke (CA)

( * ) Notice: Subject to any disclaimer, the term of this patent is extended or adjusted under 35 U.S.C. 154(b) by 541 days.

(21) Appl. No.: 16/420,019

(22) Filed: May 22, 2019

(65) Prior Publication Data

US 2019/0365208 A1 Dec. 5, 2019

Related U.S. Application Data

(60) Provisional application No. 62/679,490, filed on Jun. 1, 2018.

(51) Int. Cl.
- A61B 1/00 (2006.01)
- A61B 1/233 (2006.01)
- A61B 1/273 (2006.01)

(52) U.S. Cl.
CPC .......... *A61B 1/00135* (2013.01); *A61B 1/233* (2013.01); *A61B 1/2733* (2013.01)

(58) Field of Classification Search
CPC .. A61M 2025/0675; A61M 2025/0188; A61M 2025/1081; A61M 25/0662; A61M 25/0668; A61B 1/00135; A61B 1/00142; A61B 1/00154; A61B 1/233; A61B 1/2733; A61B 1/31
See application file for complete search history.

(56) References Cited

U.S. PATENT DOCUMENTS

| | | | | |
|---|---|---|---|---|
| 3,794,091 A | * | 2/1974 | Ersek | A61B 1/00142 385/115 |
| 4,166,469 A | * | 9/1979 | Littleford | A61M 25/007 604/164.05 |
| 4,167,939 A | * | 9/1979 | Storz | A61B 1/31 600/184 |
| 4,175,564 A | * | 11/1979 | Kwak | A61J 15/0026 604/540 |
| 4,306,562 A | * | 12/1981 | Osborne | A61M 25/0668 604/164.11 |

(Continued)

FOREIGN PATENT DOCUMENTS

| | | |
|---|---|---|
| EP | 1278571 B1 | 9/2013 |
| JP | 11276421 | 10/1999 |

(Continued)

OTHER PUBLICATIONS

Extended European Search Report for European Patent Application No. 19811470.4 dated Jan. 19, 2022.

(Continued)

*Primary Examiner* — Ryan N Henderson
(74) *Attorney, Agent, or Firm* — McCarter & English, LLP; James M. Smedley; Alex Korona

(57) ABSTRACT

The present invention generally relates to a medical device and a method of using a medical device. Specifically, the invention relates to a tube introducing device designed to introduce catheters, endoscopes and the like medical devices into organs and body lumens during procedures such as esophageal manometry, esophageal pH tests, and the placement of trans-nasal feeding tubes and a method of use thereof.

6 Claims, 2 Drawing Sheets

(56) References Cited

U.S. PATENT DOCUMENTS

| | | | | |
|---|---|---|---|---|
| RE31,855 E * | 3/1985 | Osborne | A61M 25/0668 604/161 |
| 4,596,559 A * | 6/1986 | Fleischhacker | A61M 25/0668 604/161 |
| 4,687,470 A * | 8/1987 | Okada | A61M 25/02 604/270 |
| 4,801,294 A * | 1/1989 | Okada | A61M 25/02 604/161 |
| 4,983,168 A * | 1/1991 | Moorehead | A61M 25/0668 604/161 |
| 5,158,545 A * | 10/1992 | Trudell | A61F 2/958 604/164.11 |
| 5,312,355 A * | 5/1994 | Lee | A61M 25/0668 604/161 |
| 5,320,602 A * | 6/1994 | Karpiel | A61M 25/0668 600/101 |
| 5,397,311 A * | 3/1995 | Walker | A61M 25/0668 604/160 |
| 5,429,118 A * | 7/1995 | Cole | A61B 1/00142 600/121 |
| 5,951,518 A * | 9/1999 | Licata | A61M 25/0097 604/161 |
| 6,080,141 A * | 6/2000 | Castro | A61M 25/0668 604/164.01 |
| 6,599,237 B1 * | 7/2003 | Singh | A61B 1/0008 600/114 |
| 6,712,791 B2 * | 3/2004 | Lui | A61M 39/06 604/167.04 |
| 6,758,854 B1 * | 7/2004 | Butler | A61M 39/06 604/101.01 |
| 6,808,509 B1 * | 10/2004 | Davey | A61M 25/0668 604/167.04 |
| 6,994,667 B2 * | 2/2006 | Singh | A61B 1/07 600/105 |
| 7,014,626 B2 * | 3/2006 | Sanderson | A61M 25/0668 604/164.05 |
| 7,604,627 B2 * | 10/2009 | Kojouri | A61J 15/0003 604/516 |
| 7,985,232 B2 * | 7/2011 | Potter | A61B 17/3421 606/129 |
| 7,993,305 B2 * | 8/2011 | Ye | A61M 25/0668 604/167.03 |
| 8,043,263 B2 * | 10/2011 | Helgeson | A61M 39/0606 604/161 |
| 10,827,909 B2 * | 11/2020 | Bashour | A61B 1/00082 |
| 2004/0030319 A1 | 2/2004 | Korkor et al. | |
| 2004/0102804 A1 * | 5/2004 | Chin | A61B 17/00008 606/151 |
| 2004/0186349 A1 * | 9/2004 | Ewers | A61B 1/00148 600/114 |
| 2005/0010238 A1 * | 1/2005 | Potter | A61M 39/0606 606/129 |
| 2005/0085691 A1 * | 4/2005 | Nakao | A61B 1/0125 600/128 |
| 2005/0085841 A1 | 4/2005 | Eversull et al. | |
| 2005/0177025 A1 * | 8/2005 | Jaker | A61B 1/00135 600/121 |
| 2006/0052662 A1 * | 3/2006 | Kress | A61B 1/0008 600/153 |
| 2006/0063972 A1 * | 3/2006 | Chang | A61B 1/31 600/114 |
| 2006/0167417 A1 | 7/2006 | Kratz et al. | |
| 2007/0265569 A1 * | 11/2007 | Kojouri | A61M 25/0668 604/164.01 |
| 2007/0287885 A1 * | 12/2007 | Brown | A61B 1/00142 600/107 |
| 2008/0051717 A1 | 2/2008 | Voss et al. | |
| 2009/0018508 A1 * | 1/2009 | Fisher | A61M 25/0668 604/167.04 |
| 2009/0143739 A1 * | 6/2009 | Nardeo | A61M 39/0693 604/167.04 |
| 2009/0234290 A1 * | 9/2009 | Fisher | A61M 39/0693 604/167.04 |
| 2010/0057185 A1 | 3/2010 | Melsheimer et al. | |
| 2010/0063358 A1 * | 3/2010 | Kessler | A61B 1/00142 600/121 |
| 2010/0100044 A1 * | 4/2010 | Ye | A61M 25/0668 604/167.03 |
| 2010/0280318 A1 * | 11/2010 | Chang | A61B 1/00154 600/114 |
| 2011/0251458 A1 * | 10/2011 | Terliuc | A61B 1/00082 600/116 |
| 2011/0319713 A1 * | 12/2011 | Frassica | A61B 1/00148 600/114 |
| 2012/0010468 A1 * | 1/2012 | Afridi | A61B 1/00142 600/121 |
| 2016/0001042 A1 * | 1/2016 | Worley | A61M 25/01 604/500 |
| 2016/0081537 A1 * | 3/2016 | Farhadi | A61B 1/2736 600/115 |
| 2016/0310270 A1 | 10/2016 | Nguyen et al. | |
| 2018/0296804 A1 * | 10/2018 | Bierman | A61M 39/0247 |
| 2018/0344987 A1 * | 12/2018 | Lancette | A61M 25/0668 |
| 2019/0192827 A1 * | 6/2019 | Cicalis | C08L 23/06 |
| 2019/0224449 A1 * | 7/2019 | Traxler | A61M 25/0043 |
| 2019/0246883 A1 * | 8/2019 | Bashour | A61B 1/00082 |
| 2019/0269890 A1 * | 9/2019 | Bierman | A61M 29/00 |
| 2020/0038643 A1 * | 2/2020 | Bierman | A61M 39/02 |

FOREIGN PATENT DOCUMENTS

| | | |
|---|---|---|
| JP | 2018518221 | 7/2018 |
| WO | 2018092386 | 5/2018 |

OTHER PUBLICATIONS

[Translation] Japanese Patent Office, Notice of Reasons for Rejection, dated Apr. 18, 2023.

* cited by examiner

CATHETER AND TUBE INTRODUCER

CROSS-REFERENCE TO RELATED APPLICATIONS

This application claims the benefit of U.S. Provisional Application No. 62/679,490, filed Jun. 1, 2018, the entire disclosure of which is hereby incorporated by reference in their entirety.

FIELD OF THE INVENTION

The present invention generally relates to a medical device and a method of using a medical device. Specifically, the invention relates to a tube introducing device designed to introduce catheters, endoscopes and similar medical devices into organs and body lumens during procedures, such as esophageal manometry, esophageal pH tests, and placement of trans-nasal feeding tubes and a method of use thereof.

BACKGROUND

Many medical devices have been developed for intracorporeal use. Generally, elongated tubular devices are used to facilitate navigation through, for possible treatment within, the anatomy of a patient. A variety of elongate and tubular medical devices such as catheters, probes, tubes and the like have been developed, having their advantages and disadvantages. An inherent disadvantage posed by traditional catheters and similar tubular devices, and the placement procedures for such devices, is the lack of visualization during the placement process. The inability to view where the catheter or similar tubular device is being placed can cause patients to experience unnecessary levels of discomfort during various procedures requiring the insertion of catheters and similar tubes into the mouth, nasal cavity, or esophagus.

Therefore, there is a need in the art for an introducer device, compatible with both visual examination medical devices such as endoscopes and other medical devices, to facilitate the stabilized insertion of the medical devices which may not be equipped with visualization capabilities such as catheters, esophageal probes, tubes and the like medical devices into body lumens and organs to decrease patients' discomfort during various intracorporeal procedures. These and other features and advantages of the present invention will be explained and will become obvious to one skilled in the art through the summary of the invention that follows.

SUMMARY OF THE INVENTION

The present invention is a medical device and a method of manufacture and use thereof. In some embodiments, the introducer device primarily includes an elongated tubular member engageable with the outer portion of medical devices such as endoscopes, probes, catheters and tubes.

According to embodiments of the present invention, an introducer device comprises an elongated tubular body having a substantially circular wall with an interior surface that defines an interior chamber extending from a first opening formed at an end of a first body portion of the tubular body to a second opening formed at an end of a second body portion of the tubular body, wherein the interior chamber is adapted to receive a medical device and the first body portion is more pliable than the second portion.

According to embodiments of the present invention, the elongated tubular body may be configured to be at least partially separable into two substantially semi-circular halves.

BRIEF DESCRIPTION OF THE DRAWINGS

Accompanying this written specification is a collection of drawings of exemplary embodiments of the present invention. One of ordinary skill in the art would appreciate that these are merely exemplary embodiments, and additional and alternative embodiments may exist and still be within the spirit of the invention as described herein.

DETAILED SPECIFICATION

Figure 1:
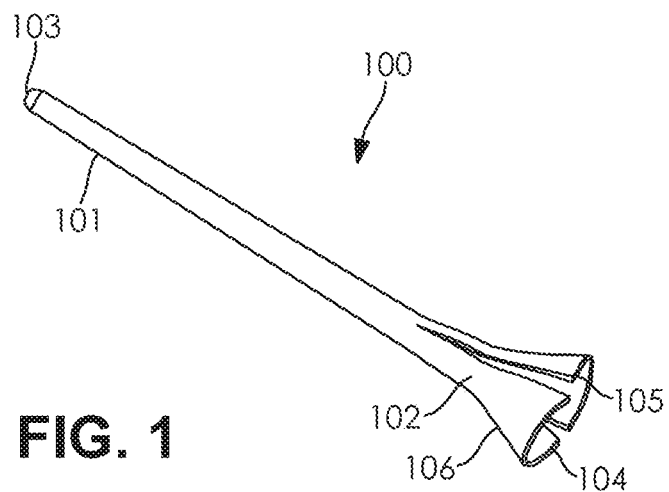
FIG. 1 shows a front perspective view of an introducer device, in accordance with an embodiment of the present invention.

The present invention generally relates to an introducer device comprised of an elongated tubular body, engageable with the outer portion of endoscopes, catheters, tubes, esophageal probes and the like medical devices.

Endoscopes, catheters, and similar elongate tubular devices are utilized during medical procedures performed by healthcare professionals, such as doctors and surgeons, to examine patients' internal organs and vessels. Endoscopic procedures that utilize natural body openings, such as the mouth and nasal cavity, to visualize, examine, and/or operate on inner organs include esophagogastroduodenoscopy (EGDs), bronchoscopy, enteroscopy, laryngoscopy, and nasopharyngoscopy.

A variety of medical procedures utilizing natural body openings, such as esophageal pH tests, esophageal manometry and the implantation of trans-nasal feeding tubes require the insertion of elongate tubular devices into a patient's mouth or nasal cavity and are performed without the visualization aide of an endoscope. These and similar procedures entail the insertion of a catheter or the like elongate tubular device into a patient's mouth, nasal cavity, or esophagus. Once inserted through the mouth or nasal cavity in accordance with the protocol for the given procedure, the medical device utilized during such procedures allows health care professionals, including doctors, to examine, treat, and/or operate on organs and lumens such as the gastrointestinal (GI) tract, including the esophagus and stomach.

Traditionally, during procedures requiring the insertion of medical devices into a patient's oral or nasal cavities or esophagus, a physician will place a catheter or similar medical device inside a patient's nasal cavity or mouth and, without the ability to visualize or know the device's exact location, the physician will continuously insert the tubular device until the device reaches a barrier in the patient's body, for example the post-pharyngeal wall in procedures where the insertion is through the patient's nose. Because this process is performed without the use of an endoscope providing visualization, the device must be maneuvered around until the physician believes the device is located inside the patient's pharynx. Without knowing the exact location of the medical device along the patient's pharynx, the physician asks the patient to initiate multiple attempts to swallow the device, while the physician pushes the device forward. Multiple swallow attempts are initiated until the device is finally swallowed, leading to the insertion of the device into the patient's esophagus. Embarking on this procedure without an endoscope or the ability to visualize the location of the medical device makes the process of inserting the catheter, esophageal probe, tube or similar medical device through the mouth or nasal cavity and into the esophagus uncomfortable, and at times intolerable, to patients whose medical care requires adherence to examinations and procedures such as these. Moreover, the attempted placement of the medical device without functional visualization may be a dangerous procedure for patients, as the medical device may be mistakenly inserted into the patient's trachea instead of the patient's esophagus. Thus, an introducer device in accordance with embodiments of the present invention is needed to couple with medical devices such as endoscopes having visualization functionalities and other medical devices, such as catheters, manometry probes and similar probes or elongate medical devices or portions of these and other medical devices, to allow for visualization prior to the insertion of medical devices, and enable the easy and comfortable insertion of such medical devices into the esophagus through the mouth or nose.

It is an aspect of the present invention to provide an introducer device, configured to couple with both endoscope devices having visualization capabilities and other medical devices, including medical devices lacking visualization capabilities. For example, the introducer device may couple with endoscopes to enable physicians to insert the introducer device and the endoscope into the esophagus of a patient, while visualizing the insertion process. Once the introducer device and the endoscope are inserted into the esophagus to the desired extent, the physician is able to retract the endoscope from within the introducer device, and insert a second medical device, for example, a medical device lacking visualization capabilities, into the introducer device to examine, treat, or conduct tests on the desired organs and lumens, such as the esophagus, located within the anatomy of the patient.

Embodiments of the present invention are generally directed to an introducer device comprising an elongated tubular member, engageable with the outer portion of both endoscopes and other medical devices, allowing, in one respect, for visualization during the insertion of an endoscope or similar visualization device into the esophagus through the nose or mouth, and in a second respect, the retraction of the endoscope while the position of the introducer device is maintained, allowing for the introduction of a second medical device into the desired body lumen through the introducer device which has been placed in the desired body lumen or organ with visualization.

The various embodiments of the introducer are designed to make the introduction of both the introducer and other medical devices into the esophagus more comfortable and tolerable for patients. Furthermore, the novel construction of the introducer decreases the number of unsuccessful and painful swallow attempts previously required in order for traditional intracorporeal medical devices to be swallowed by the patient.

In accordance with several embodiments of the present invention, a first body portion of the introducer may be comprised of a substantially pliable and elastic material and a second body portion may be comprised of a substantially rigid material. In some embodiments, the first and second body portions are formed of the same material, wherein the first body portion is formed from one layer of the material, while the second body portion is formed from several layers of the material, rendering the second body portion more rigid than the first body portion. In several embodiments of the present invention, the first body portion of the introducer device and the second body portion of the introducer device collectively form a single continuous and substantially hollow tube, thereby providing a first opening formed at the first body portion of the introducer device and a second opening formed at the second body portion of the introducer device. In a preferred embodiment, the first body portion of the introducer device is configured to be the portion of the introducer device that is first inserted into the patient and therefore the portion of the introducer device that will be the most internal within the patient. Conversely, the second body portion of the introducer device is generally configured to first receive the medical device and to be the portion of the introducer device that remains external to the patient at all times.

In an embodiment of the present invention, both the first and second body portions of the introducer device facilitate engagement with endoscopes and other medical devices for introduction of the medical devices into organs or body lumens during various intracorporeal procedures. In other embodiments, only one of either the first or second body portions engages with the endoscopes and other medical device for introduction of the endoscope and the medical device into organs or body lumens during various intracorporeal procedures.

According to some embodiments of the present invention, the first body portion of the introducer device is formed out of elastic and pliable material to facilitate fluid engagement of the introducer device with organs and lumens such as the esophagus, through which a medical device such as an endoscope, catheter, manometry probe, tube or other medical device or a portion of a medical device is intended to travel, thereby improving patient comfort and facilitating smooth and stable engagement of the devices during the insertion process. Furthermore, the elastic and pliable material forming the first body portion of the introducer device allows it to take advantage of the articulation functionality of an endoscope to place the device. In some embodiments, the articulating force imparted by the endoscope can be used to bend the tip of the first body portion of the introducer device in a desired direction to further ease the placement of the introducer device.

According to an embodiment of the present invention, the introducer device may include a separation element along opposing side walls of both the first and second body portions, making the introducer separable into two substantially semi-circular halves. In accordance with embodiments of the present invention, the separation element may be a slit. In some embodiments, the separation element may be a groove. In some embodiments, the separation element may be a perforated line. In some embodiments, the separation element may be a corrugated line. In some embodiments, the separation element may be a substantially thin layer of the same or similar material used to create the introducer device. In some embodiments, only the first body portion of the introducer device includes a separation element along its opposing sidewalls, making the first body portion separable into two substantially semi-circular halves. In some embodiments, only the second body portion of the introducer device includes a separation element along its opposing sidewalls, making the second body portion separable into two substantially semi-circular halves. In any embodiment, the separation element aids in the detachment of the introducer device from a medical device such that the introducer device can be removed from over the medical device while the medical device is maintained within the patient, without necessitating the removal of the medical device or causing its displacement.

According to an embodiment of the present invention, the exterior surface of the introducer device is composed of a material having a lower coefficient of friction than an endoscope or other medical device, to reduce the amount of discomfort associated with the traditional procedure of inserting the medical devices into the patient. In some embodiments, the opening at the end of the first body portion is rounded or curved to mitigate patient discomfort when the introducer device is inserted into a body lumen.

According to an embodiment of the present invention, the second opening of the introducer device includes a flare end, having a conical profile to aide in the insertion of the introducer device into a patient's nasal cavity. In some embodiments the conical profile includes a notch or indent. In situations where the introducer device is used in conjunction with medical devices intended for introduction into the body through a patients' nasal cavity, the flare or conical profile prevents the introducer device from being inserted more than necessary into the nasal passageway. For example, a nasopharyngoscope, or similar endoscope intended for introduction through a patients' nasal cavity, and the introducer device are advanced as far as possible until the flare end of the introducer device is placed at the distal end of the nasal passageway. Once the introducer device, coupled to the endoscope, is advanced as far as permitted by the flare end, the endoscope is retracted from within the introducer device so that a second medical device may be inserted into the patient, through the opening in the introducer device.

According to embodiments of the present invention, the flare at the second opening of the introducer device may be attached to a holder configured to hold the introducer device. In another embodiment, the holder facilitates the insertion of the introducer device into the desired body lumen.

Figure 2:
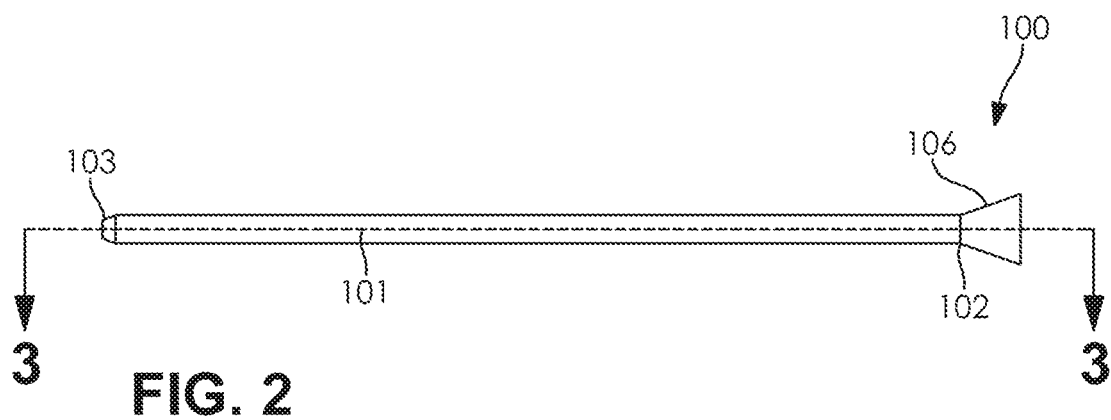
FIG. 2 shows a side view of an introducer device, in accordance with an embodiment of the present invention.
Figure 3:
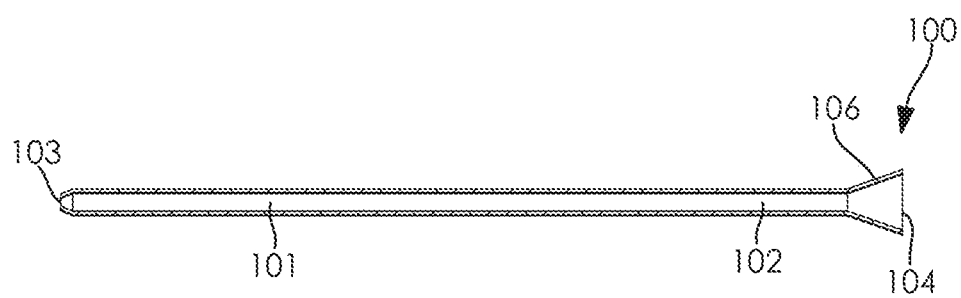
FIG. 3 shows a cross sectional view of an introducer device, in accordance with an embodiment of the present invention.

Turning to FIGS. 1-4, a medical device, in accordance with an embodiment of the present invention, is shown. As shown in FIG. 1-3, the introducer device 100 comprises a first body portion 101 and a second body portion 102. The first body portion 101 may be greater in length than the second body portion 102. As shown in FIG. 1, the first body portion 101 and the second body portion 102 collectively form a single continuous and substantially hollow tube, provided with a first opening 103 formed at an end of the first body portion 101 and a second opening 104 formed at an end of the second body portion 102. In some embodiments, the first body portion 101 is formed of a pliable and elastic material, while the second body portion 102 is formed of a substantially rigid material. In some embodiments, the first and second body portions 101 and 102 are formed of the same material, wherein the first body portion 101 is formed from one layer of the material, while the second body portion 102 is formed from several layers of the material, rendering the second body portion 102 more rigid than the first body portion 101. In some embodiments, the second opening 104 at the second body portion 102 of the introducer device 100 may include a flare end. In some embodiments, at least a portion of the introducer device is formed from a polyvinyl chloride (PVC) material. In some embodiments, at least a portion of the introducer device is formed from a polycarbonate (PC) material.

In accordance with several embodiments of the present invention, the first body portion 101 is configured to be the portion of the introducer device 100 that is first inserted into the patient and therefore the portion of the introducer device 100 that will be the most internal within the patient. Conversely, the second body portion 102 of the introducer device 100 is generally configured to first receive a medical device and to be the portion of the introducer device 100 that remains external to the patient at all times.

In an embodiment of the present invention, both the first body portion 101 and the second body portion 102 of the introducer device 101 facilitate engagement with medical devices such as endoscopes, tubes, probes, catheters and the like for introduction of medical devices such as endoscopes in a first instance and other medical devices such as tubes, probes and catheters in a second instance to introduce these medical devices into organs or body lumens during various intracorporeal procedures. In other embodiments, only one of either the first body portion 101 or the second body portion 102 engages with the medical devices for introduction of a chosen medical device and the introducer device 100 into organs or body lumens during various intracorporeal procedures. In some embodiments, the introducer device 100 is greater in length than the probe or tube of an endoscope or other medical device. In some embodiments, the introducer device 100 is shorter in length than the probe or tube of an endoscope or other medical device.

According to an embodiment of the present invention, the introducer device may include a separation element 105 along opposing side walls of both the first body portion 101 and the second body portion 102, making the introducer device 100 separable into two substantially semi-circular halves. In accordance with embodiments of the present invention, the separation element 105 may be a slit. In some embodiments, the separation element 105 may be a groove. In some embodiments, the separation element 105 may be a perforated line. In some embodiments, the separation element 105 may be a corrugated line. In some embodiments, the separation element 105 may be a substantially thin layer of the same or similar material used to create the introducer device 100. In some embodiments, only the first body portion 101 of the introducer device 100 includes a separation element 105 along its opposing sidewalls, making the first body portion 101 separable into two substantially semi-circular halves. In some embodiments, only the second body portion 102 of the introducer device 100 includes a separation element 105 along its opposing sidewalls, making the second body portion 102 separable into two substantially semi-circular halves. In any embodiment, the separation element 105 aids in the detachment of the introducer device 100 from a medical device such that the introducer device 100 can be removed from over the medical device while the medical device is maintained within the patient, without necessitating the removal of the medical device or causing its displacement.

According to an embodiment of the present invention, the exterior surface of the introducer device 100 is comprised of a material having a lower coefficient of friction than a medical device such as an endoscope, to reduce the amount of discomfort associated with the traditional procedure of inserting the medical device into the patient.

According to an exemplary embodiment of the present invention, the second opening 104 of the introducer device 100 may have a flared end 106. In some embodiments, the flared end 106 has a conical profile to aide in the insertion of the introducer into a patient's nasal cavity. In some embodiments, the conical profile may have a notch or dent. In situations where the introducer device 100 is used in conjunction with medical devices intended for introduction into the body through a patients' nasal cavity, the flare or conical profile prevents the introducer device from being inserted more than necessary into the nasal passageway. For example, a nasopharyngoscope, or similar endoscope intended for introduction through a patients' nasal cavity and the introducer device 100 are advanced as far as possible until the flare end of the introducer device 100 is placed at the distal end of the nasal passageway. Once the introducer device 100, coupled to the endoscope, is advanced as far as permitted by the flare end, the endoscope is retracted from within the introducer device 100 so that a second medical device such as a tube, catheter or other probe may be inserted into the patient, through the introducer device 100.

In some embodiments, the flare at the second opening 104 of the introducer device 101 is attached to a holder, meant for holding the introducer device 101. In some embodiments, the holder facilitates the insertion of the introducer device into the desired body lumen.

Figure 4A:
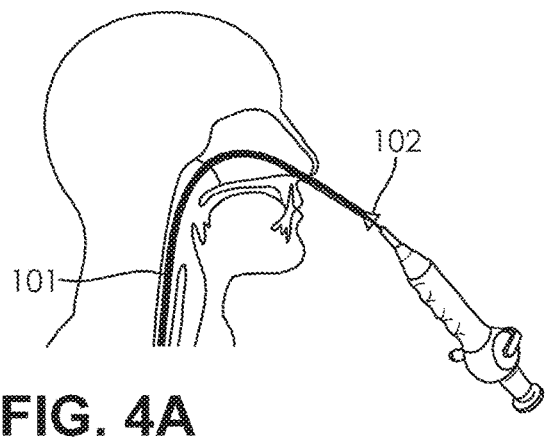
FIG. 4A is a diagram demonstrating a use of the introducer device, wherein a nasopharyngoscope has been utilized to insert the introducer device into a patient's body under visualization, in accordance with an embodiment of the present invention.
Figure 4B:
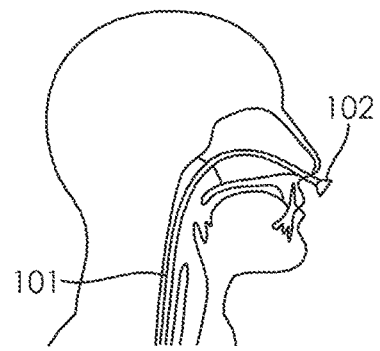
FIG. 4B is a diagram demonstrating a use of the introducer device, wherein the introducer device is positioned within a patient's body, in accordance with an embodiment of the present invention.

As demonstrated by FIG. 4A, the introducer device 100 may be utilized by inserting an endoscope into and through the introducer device 100. The introducer device 100 may be shorter in length than the probe of the medical device such that the end of the probe is not covered by the device 100 when the devices are coupled to each other. The endoscope may be turned on to activate the visualization protocols of the device such as video imaging and light production. The endoscope coupled to the introducer device 100 may then be inserted into the body. The introducer device 100 may bend as necessary during the insertion process. For example, if the introducer device 100 is being inserted through a patient's nose, the introducer device 100, along with the endoscope will travel into the patient's nose and bend in order to continue traveling through the patient's throat and down the patient's esophagus. The introducer device 100 may be inserted into the body to the extent necessary or desired by the healthcare professional. As demonstrated by FIG. 4B, the endoscope may be disengaged from the introducer device 100 and removed, while the introducer device 100 maintains it general position in the patient's body.

Figure 4C:
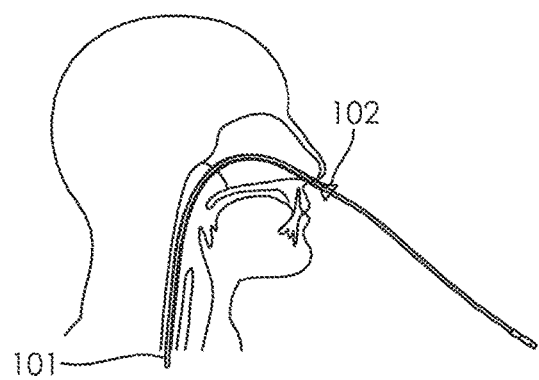
FIG. 4C is a diagram demonstrating a use of the introducer device, wherein a second medical device, namely, a manometry probe, has been inserted into the introducer device for entry into a patient's body, in accordance with an embodiment of the present invention.
Figure 4D:
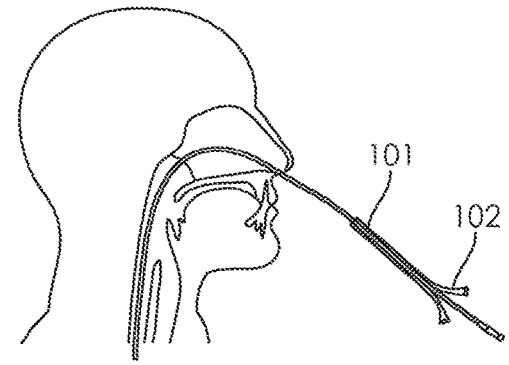
FIG. 4D is a diagram demonstrating a use of the introducer device, wherein the introducer device is removed from within a patient's body while a second medical device, namely, a manometry probe, maintains its general position within the patient's body, in accordance with an embodiment of the present invention.

As demonstrated by FIG. 4C, after installation of the introducer device 100 with the aide of an endoscope, a probe of a second medical device may be easily inserted into the body through the introducer device 100. As demonstrated by FIG. 4D, once the medical device is placed in the appropriate position, as determined by the health professional, the introducer device 100 may be removed from the body by sliding the introducer device 100 off the medical device and out of the body, while the medical device maintains its general position within the body. Once the introducer device 100 is external to the body, the introducer device 100 may be disengaged and removed from around the medical device by splitting the introducer device 100 into two substantially semicircular halves by slicing the introducer device 100 separation element 105 provided on the opposing side walls of the introducer device 100.

According to embodiments of the present invention, an introducer device 100 comprises an elongated tubular body having a substantially circular wall with an interior surface that defines an interior chamber extending from a first opening 103 formed at an end of a first body portion 101 of the tubular body to a second opening 104 formed at an end of a second body portion 102 of the tubular body, wherein the interior chamber is adapted to receive a medical device and the first body portion is more pliable than the second portion. In some embodiments, the elongated tubular body may be configured to be at least partially separable into two substantially semi-circular halves.

The terminology used herein is for the purpose of describing particular embodiments only and is not intended to be limiting of the invention. As used herein, the term "and/or" includes any and all combinations of one or more of the associated listed items. It will further be understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature and not restrictive.

What is claimed is:

1. An introducer device for introduction of one or more medical devices into a patient esophagus through a patient nasal cavity, comprising:

an elongated tubular body having a substantially circular interior wall that defines an interior chamber extending from a first opening formed at first body portion of the tubular body to a second opening formed at second body portion of the tubular body, with the second body portion terminating at an end portion formed in the shape of a cone having an exterior wall specifically configured to fit within a patient nasal cavity, wherein an edge of the first body portion end is curved along its perimeter to form a rounded tip within which the first opening is disposed, the rounded tip specifically configured to enhance patient comfort during introduction of the introducer device into or through the patient gastrointestinal system, wherein the diameter of the interior chamber is of sufficient size to receive an esophageal endoscope and enables visualized introduction of the introducer device through the first opening of the tubular body to support placement of at least the first body portion of the introducer device into an introduced position within the patient esophagus, wherein at least the first body portion of the introducer device remains in the first introduced position while the esophageal endoscope is removed and a second medical device is introduced to the introduced position, and wherein the second opening of the tubular body provides a user with access into the interior chamber to grasp and pull a portion of the interior wall to separate the tubular body into two substantially semi-circular halves to support removal of the introducer device from within the patient while permitting the second medical device to remain in the introduced position.

2. The introducer device for introduction of one or more medical devices into a patient esophagus of claim 1, wherein the rounded tip enhances patient comfort by reducing irritation of the patient esophageal sphincter.

3. The introducer device for introduction of one or more medical devices into a patient esophagus of claim 1, wherein the first body portion is formed of a first material and the second body portion is formed of a second material, the first material is flexible and sufficiently rigid to support the first body portion maintaining a substantially tubular shape when at least a section of the first body portion is within an upper esophageal sphincter, and the second material is more rigid than the first material.

4. The introducer device for introduction of one or more medical devices into a patient esophagus of claim 1, wherein the rounded tip prevents the introducer device from irritating the patient post pharyngeal wall.

5. The introducer device for introduction of one or more medical devices into a patient esophagus of claim 1, wherein a scope portion of the esophageal endoscope has an internal tubular diameter of at least 4 mm.

6. The introducer device for introduction of one or more medical devices into a patient esophagus of claim 1, wherein the cone comprises a pair of opposing notches, each extending towards a perforation line to enable separation of the tubular body into the two substantially semi-circular halves.

* * * * *